(12) United States Patent
Biegun et al.

(10) Patent No.: US 11,033,405 B2
(45) Date of Patent: Jun. 15, 2021

(54) DEVICE FOR GRIPPING AND INSERTING AN INSERT ELEMENT

(71) Applicant: XNOV IP, Luxembourg (LU)

(72) Inventors: Jean-François Biegun, Porrentruy (CH); Frédérique Biegun, Porrentruy (CH); Pascal Loehle, Porrentruy (CH)

(73) Assignee: XNOV IP, Luxembourg (LU)

( * ) Notice: Subject to any disclaimer, the term of this patent is extended or adjusted under 35 U.S.C. 154(b) by 43 days.

(21) Appl. No.: 16/218,622

(22) Filed: Dec. 13, 2018

(65) Prior Publication Data

US 2019/0110904 A1 Apr. 18, 2019

Related U.S. Application Data

(62) Division of application No. 14/640,212, filed on Mar. 6, 2015, now abandoned.

(30) Foreign Application Priority Data

Mar. 7, 2014 (FR) ..................... 14 00564

(51) Int. Cl.
*A61F 2/46* (2006.01)
*A61F 2/34* (2006.01)
*A61F 2/30* (2006.01)

(52) U.S. Cl.
CPC .......... *A61F 2/4609* (2013.01); *A61F 2/4637* (2013.01); *A61F 2/34* (2013.01);
(Continued)

(58) Field of Classification Search
CPC . A61B 34/20; A61B 17/1659; A61B 17/1668; A61B 2090/031; A61F 2/4609;
(Continued)

(56) References Cited

U.S. PATENT DOCUMENTS 6,468,281 B1 10/2002 Badorf et al. .................. 606/91
2007/0219562 A1* 9/2007 Slone ....................... A61F 2/34
606/99
(Continued)

FOREIGN PATENT DOCUMENTS

FR 3028173 A1 * 5/2016 ........... A61F 2/4637
WO WO 2008/106598 A1 9/2008
WO WO 2011/161166 A1 12/2011

OTHER PUBLICATIONS

French Search Report dated Nov. 4, 2014 in related application No. FR1400564.
(Continued)

*Primary Examiner* — Ann Schillinger
(74) *Attorney, Agent, or Firm* — Renner Kenner Greive Bobak Taylor & Weber Co., LPA

(57) ABSTRACT

A device for a cup to be received in the cotyl of a hip. The device includes an insert, a gripping means for gripping the insert, a rod for imparting shock, and an impaction head having a surface in contact with a portion of the insert. The rod for imparting shock is designed to be held by a surgeon and is used for the application of an impaction shock to the insert when held by the gripping means opposite the cup to be introduced into the cotyl of a hip. The impaction head having a surface in contact with a portion of said insert and the rod are connected to one another so as form a head and rod assembly joined in rotation. The head and rod assembly is mounted pivotably at a pivot point in relation to the gripping means.

16 Claims, 3 Drawing Sheets

(52) U.S. Cl.
CPC ............... *A61F 2002/30332* (2013.01); *A61F 2002/30378* (2013.01); *A61F 2002/30538* (2013.01); *A61F 2002/4681* (2013.01)

(58) Field of Classification Search
CPC ........ A61F 2/4657; A61F 2/34; A61F 2/4607; A61F 2002/4681; A61F 2/32; A61F 2/36; A61F 2002/4623; A61F 2002/4687; A61F 2002/4635; A61F 2002/4666; A61F 2/3859; A61F 2220/0033; A61F 2/46; A61F 2002/30405; A61F 2002/30471; A61F 2002/30507; A61F 2/3609; A61F 2002/30774; A61F 6/18; A61F 2002/3038; A61F 2002/3085; A61F 2002/30894
See application file for complete search history.

(56) References Cited

U.S. PATENT DOCUMENTS

2012/0303035 A1* 11/2012 Geebelen ................. A61F 2/34
606/91
2015/0182351 A1 7/2015 Behzadi ................ A61F 2/4609

OTHER PUBLICATIONS

Office Action dated Sep. 22, 2017 and response electronically filed thereto on Dec. 21, 2017 in related U.S. Appl. No. 14/640,212.
Office Action dated Jan. 19, 2018 and Response electronically filed thereto on May 25, 2018 in related U.S. Appl. No. 14/640,212.
Office Action dated Sep. 13, 2018 in related U.S. Appl. No. 14/640,212.

* cited by examiner

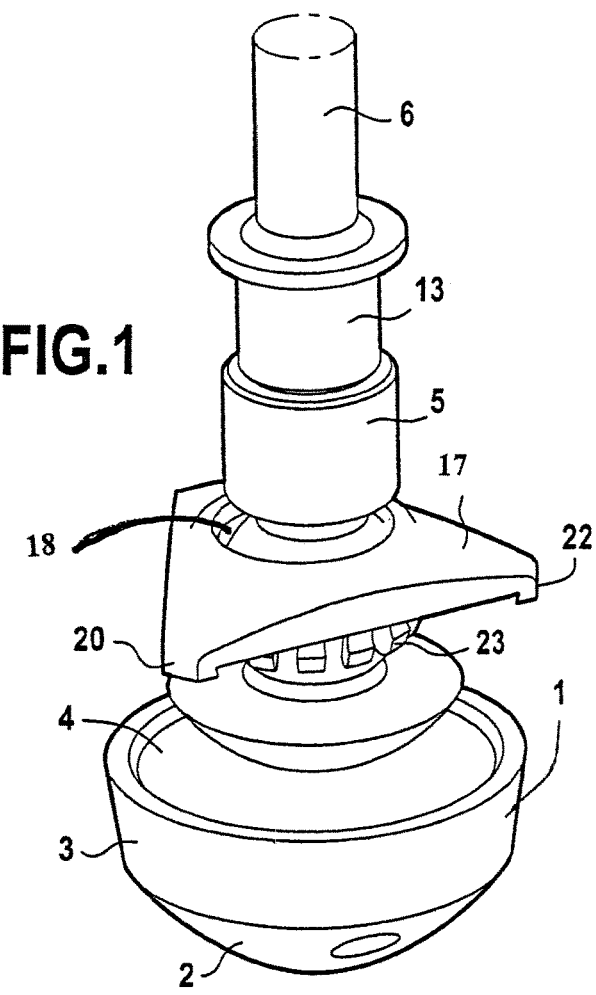
FIG.1
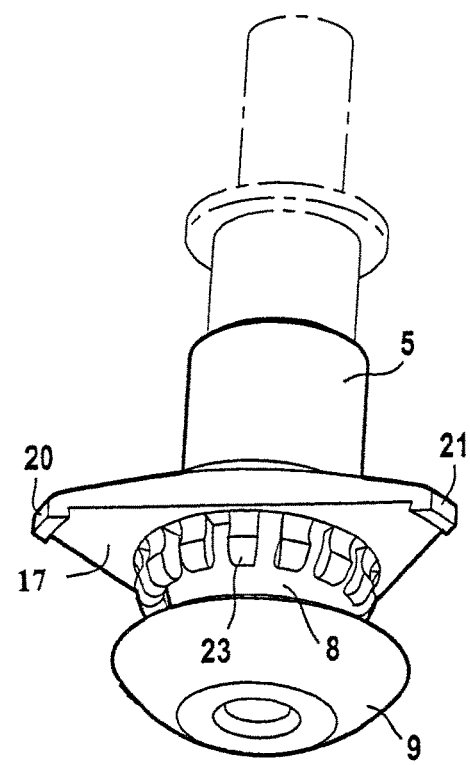
FIG.3
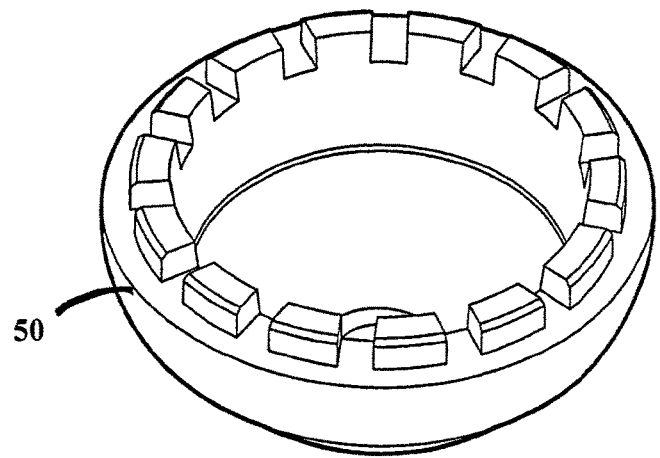

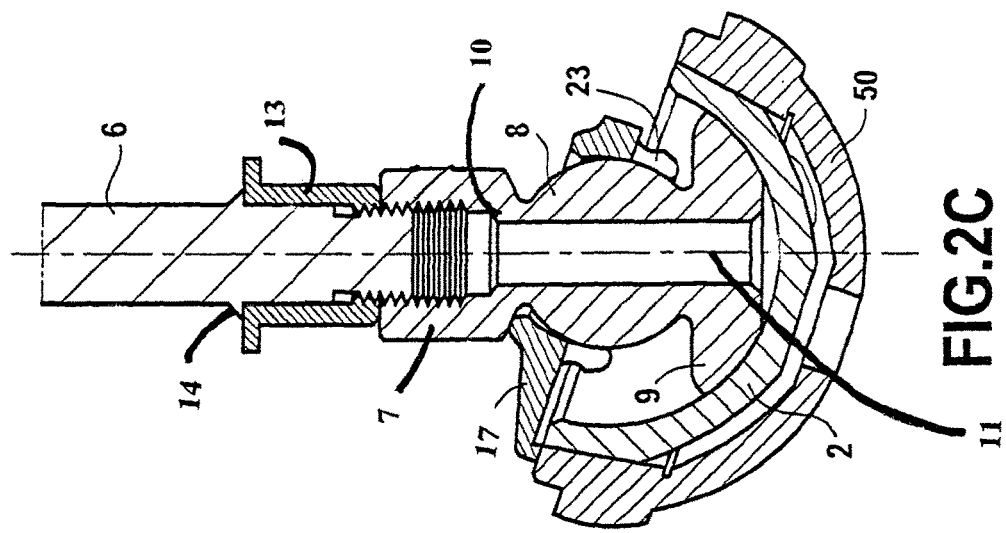
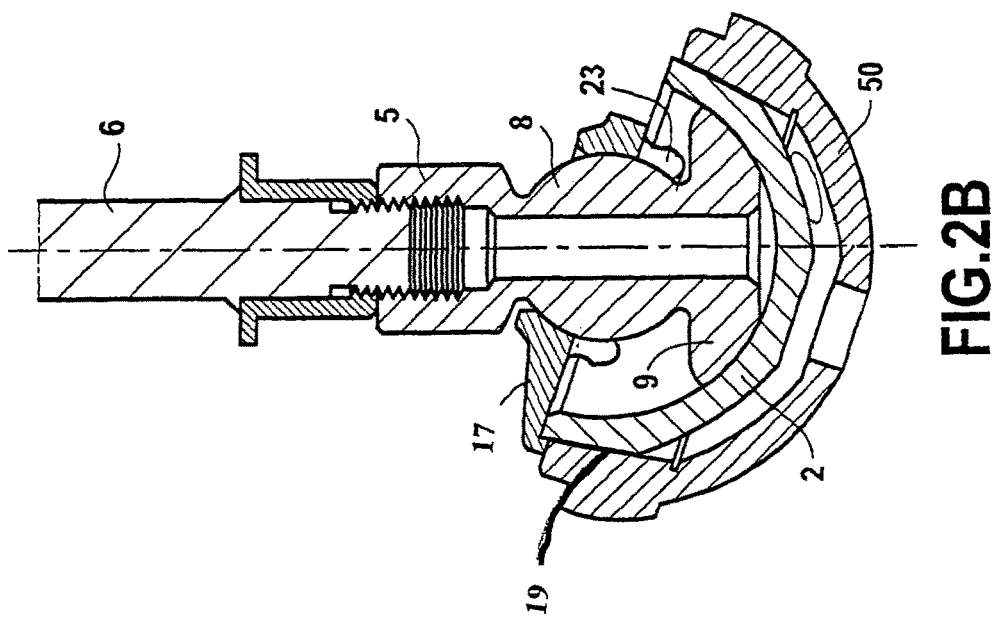
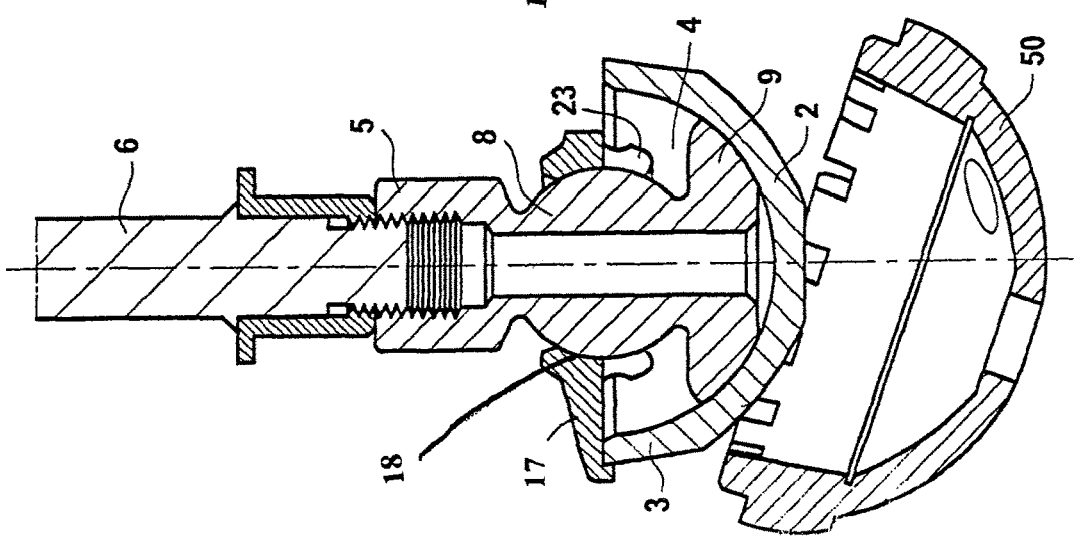

DEVICE FOR GRIPPING AND INSERTING AN INSERT ELEMENT

CROSS-REFERENCE TO RELATED APPLICATIONS

This application is a divisional application of U.S. patent application Ser. No. 14/640,212 entitled "Device for Gripping and Inserting an Insert Element" filed on Mar. 6, 2015, which is incorporated herein by reference in its entirety.

TECHNICAL FIELD

The present invention relates to a device for inserting an insert element, made in particular of ceramic material, into a cup which is itself designed to be received in the cotyloidal cavity of a hip of a patient.

BACKGROUND ART

Insertion devices are already known that comprise a rod, an impaction head fixed to the end of the rod and designed to come into contact with the insert and gripping means designed for temporarily holding the insert to the insertion device when the impaction head is in contact with the insert, the latter being then adjusted by force to the cup by means of a shock or impaction applied to the rod by the surgeon to secure it in such a way that it is difficult, almost impossible, to remove.

Said devices of the prior art are complicated to use and do not guarantee a reliable impaction force in the right direction. It is often the case that either the insert is misaligned in relation to the cup prior to its impaction, or the axis in which the impaction is performed is not set accurately in a direction suitable for joining the insert and the cup perfectly. As a result the insert could be fitted badly in the cup, which over the long term may lead to breaking and associated complications for the patient (new operation for removing the defective cup, which is often shattered, and refitting a cup).

DISCLOSURE OF THE INVENTION

The present invention proposes overcoming the disadvantages of the prior art by proposing an insertion device which makes it possible to achieve the impaction of the insert into the cup with a very precise orientation relative to the insert and the cup, thus largely avoiding its deterioration over the long term, in particular avoiding cracks or breakages, and thus guaranteeing a long lifetime for the cup in the hip.

According to the invention, a device for inserting an insert, made in particular of ceramic material, by impaction into a cup designed to be received in the cotyl of a hip, comprising:

means for gripping the insert, in particular on an upper free edge of the insert;

a shock application rod designed for the surgeon to hold and for the application of an impaction shock to the insert when it is held by gripping means opposite the hollow part of the cup so as to be introduced therein; and an impact head with a surface designed to come into contact with at least a portion of the insert, in particular the inner surface of a hollow of the insert, is characterised in that the impaction head and the application rod are connected to one another in a rotatable manner, in particular the head emerges from the rod; and the impaction head and rod assembly is mounted pivotably in relation to the gripping means of the insert, in particular in the manner of a pivot pin.

In this way an insertion device is obtained for insertion by impaction which makes it possible to perform said insertion in a particularly reliable and simple manner, by reducing to a very large degree the risk of "off-centre" insertion, which is a potential source of tearing or breaking of the cup once it has been placed into the cotyl. Whatever the angle of the force of impaction relative to the insert, i.e. the orientation of the rod relative to the insert, the latter, held by the insertion device with the possibility of pivoting, is always positioned perfectly relative to the cup, regardless of the orientation of the rod relative to the cup, such that the surgeon no longer needs, as in the prior art, to ensure that the rod is aligned perfectly perpendicularly to the plane of the base of the cup during the insertion.

Preferably, the pivot point of the assembly pivoting the gripping means relative to the rod-impaction head assembly is located substantially in the centre of the inner sphere of the insert.

According to a preferred embodiment of the invention, the gripping means of the insert are formed by a holding grip comprising at least two, preferably three, feet designed to fit around the insert in a releasable elastic manner.

Preferably, the holding grip comprises a base plate from the periphery of which the feet project.

In particular, the base plate is pierced by a hole, in particular substantially in the centre, the inner wall surface of which matches the form of a pivot pin formed on the rod so as to enable the relative pivoting of the rod and the base plate.

According to an advantageous embodiment, the distal end of the rod comprises a head projecting laterally from the rod and forming the impaction head, the head having a distal end surface, in particular in the form of a dome, designed to match in part the form of the base of the inner cavity of the insert.

Preferably, the outer surface of the impaction head 9 designed to be applied against the wall of the base of the cavity 4 is in the form of a sphere, the centre of which coincides with the pivot point.

In this way a free orientation of the insert is achieved.

According to one refinement also forming an invention in itself, independently of the invention described above, the device for inserting an insert, made in particular of ceramic material, into a cup designed to be received in the cotyl of a hip, comprising gripping means for the insert, in particular at an upper free edge of the insert, and a rod designed for the impaction of the insert when it is held by the gripping means opposite the hollow part of the cup, comprises means for imparting a downwards shock to the rod for the impaction of the insert into the cup, that is introduce it with an adjustment of force into the cup, said means for imparting a shock conveying a shock of predetermined power to the rod.

According to data and/or experience, it is also possible to adjust the power of the shock to optimise the blow given to the insert for the insertion thereof, thus avoiding variations in the power provided by the practitioner and/or his form on the day which are likely to involve either the cracking or breaking of the insert or the cup, or an incomplete insertion of the insert into the cup.

According to a preferred embodiment of the invention, the means for imparting a shock of predetermined power to the rod comprise a piston and a spring.

Preferably, means are provided for moving the piston against the compression of the spring so as to compress the spring.

According to a preferred embodiment, it is possible to provide means for locking the piston in a loaded position in which the spring is compressed and means, in particular in the form of a trigger, designed to release the piston, the release of the piston involving its instantaneous displacement by means of the decompression of the spring and its pulse action on the rod imparting to the latter a predetermined level of shock.

Preferably, the spring and the piston are received in a cavity proximal to the rod.

Preferably, the cavity receiving the piston and the spring is formed in a frame in one piece with the rod.

Preferably, a grip, in particular in the form of a pistol grip, projects laterally from the body.

The present invention also relates to an assembly comprising an insertion device according to the invention and at least one insert, made in particular of ceramic material, designed to be inserted into a cup of a cotyl, as well as to a unit comprising an assembly according to the invention and a cup designed to be received in a cotyl of a hip.

BRIEF DESCRIPTION OF THE DRAWINGS

In the following, by way of example, embodiments of the invention are described with reference to the drawings, wherein:

FIG. 1 is an insertion device according to the invention, a cup and an insert made of ceramic material designed to be inserted by the insertion device inside the cup 50;

FIGS. 2A, 2B and 2C represent the different stages of inserting the insert into the cup by means of the insertion device;

FIG. 3 is a perspective view from below of part of the insertion device of FIG. 1.

PREFERRED EMBODIMENT FOR CARRYING OUT THE INVENTION

Figure 4:
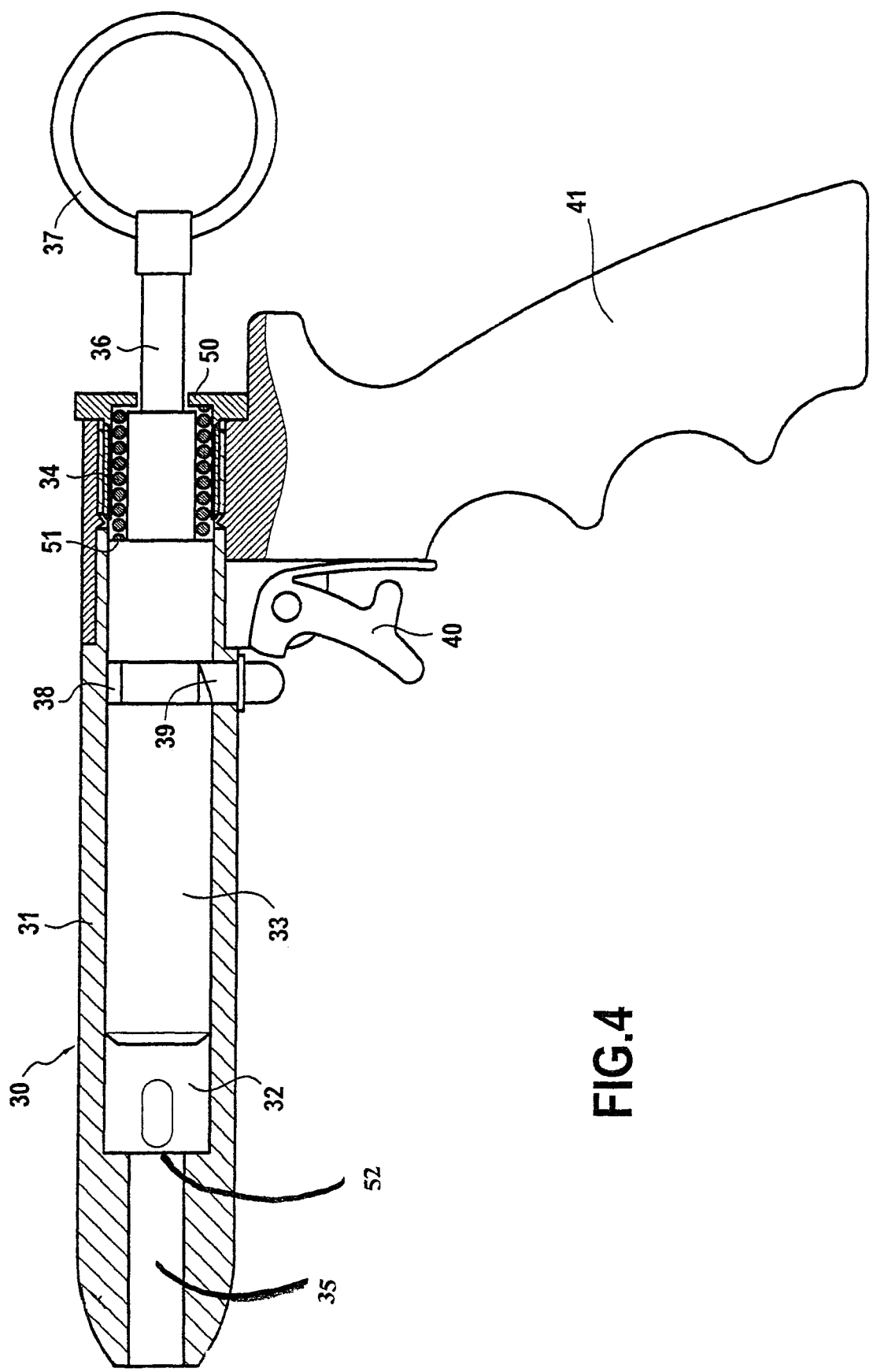
FIG. 4 is a perspective view of a device for applying a shock to the rod of the insertion device of the preceding figures which, according to an advantageous embodiment, can be adapted to the insertion device of FIGS. 1 to 3.

FIG. 1 is a perspective view of an insertion device according to an embodiment of the invention of an insert 1 made of ceramic material in a cup 50. The insert 1 made of ceramic material is formed by a ceramic body, in particular made of alumina ceramic material, with an exterior surface in the form of a spherical cap 2 terminated by a part 3 of the upper or proximal edge with a slightly truncated cone shape. The insert is hollow and comprises an inner cavity 4 the wall of which has a hemispherical form. In particular, the shaped cone of the truncated cone part 3 of the edge of the outer surface of the insert forms an angle of about 3 to 5° relative to the vertical axis of symmetry of the insert made of ceramic material.

The insertion device is formed by a circular cylindrical rod 6 to which an impaction end piece 5 has been adapted at its distal end. The end piece 5 comprises a tubular proximal section 7 which is tapped to receive the threaded end of the rod 6 therein, to thus join the latter by screw connection. It is possible instead to ensure that the end piece is held with the rod by means of another type of connection, for example a clipping system. It is also possible for the end piece to be in one piece with the rod.

The end piece 5 then comprises an intermediate section in the form of a spherical ball 8 and a distal section forming the impaction head 9. The impaction head 9 has a greater transverse dimension than the rest of the end piece 5, in particular than the proximal section 7, and its lower or distal surface is in the form of a dome being at least partly complementary to the inner surface of the cavity 4 of the insert 1, so as to be able to make surface contact with the latter. Conversely, it is also possible that the impaction head 9 has a smaller transverse dimension than the rest of the end piece 5, in particular than the proximal section 7.

The outer surface of the head 9 designed to be applied against the wall of the base of the cavity 4 is inscribed in a sphere, concentric to the sphere defining the ball 8. This facilitates the free orientation of the insert.

On the inside of the end piece 5, at the end of the proximal section 7 there is an abutment 10 against which the distal end of the rod 6 abuts, in order to block its screw connection with the internal tapping of section 7. Furthermore, a channel 11 opening to the lower surface in the form of a dome of section 9 by an opening facilitates the internal cleaning of the end piece.

A connecting element 13 which is also tubular terminates the connection between the end piece 5 and the rod 6. Said element 13 comprises a threaded end which screws into the part of the thread of the screw which does not cooperate with the tapping of the end piece 5. From the other proximal side the element 13 is welded at 14 to the rod.

An element forming a grip is mounted pivotably in relation to the ball 8. Said grip comprises a substantially planar plate 17, with a triangular form and with three tips from which three respective feet 20, 21 and 22 project. The feet are designed to fit around the insert on its upper or proximal edge. The feet and/or the plate are made from a material and/or have thickness such that they have a certain degree of elasticity which enables them to fit elastically around the upper edge of the insert 1 in an flexible manner and to release it when a deforming force is applied to the grip, for example by bearing on the plate 17. The plate 17 is pierced in its centre by a hole 18 with a shape complementary to the spherical ball 8 forming the pivot pin and comprises elements 23 in the form of teeth which have substantially a form complementary to that of the spherical ball 8 so as to match the form. The material and/or the thickness of the teeth is(are) selected so as to enable the elastic clipping of the plate onto the pivot pin. The inner edge of the hole 18 has an inner wall with a curved shape complementary to the form of the ball 8 forming the pivot pin. The assembly is such that the plate 17, once clipped by teeth 23 to the pivot pin 8, can pivot relative to the pivot pin 8, and therefore relative to the connected rod 6 particularly in rotation of the pivot pin 8.

In the embodiment shown three feet have been provided. However, it would also be possible to have more, in particular four or five for large inserts. It is also possible instead of feet to provide a disc that runs all around.

The dimension of the plate is such that when the head 9 is in contact with the surface of the internal wall of the insert made of ceramic material, the three feet 20, 21 and 22 fit around the free peripheral edge of the truncated cone part 3 of the insert 1 made of ceramic material, the three feet 20, 21 and 22 then extend towards the cup along the outer surface of the part 3 of the insert 1 made of ceramic material by fitting around the latter. The insert 1 made of ceramic material is thus held by the grip in an elastic manner.

Once the insert is held between the feet 20, 21, 22 (FIG. 2A), the insert 1 is positioned by means of the device on the inside of the cup (FIG. 2B). This stage is performed without it being necessary for the insertion axis (the axis of the rod) to be perpendicular to the base plane or upper plane of the cup or insert, by the relative pivot mounting of the grip-insert assembly previously joined mutually by clamping the feet. This second stage of pushing takes place until the distal edges of the feet 20, 21 and 22 abut against the upper free edge of the cup. At this moment, the insert is largely introduced into the cup having its truncated cone part 3 almost in contact with the inner face of the cup, in an upper section 19 having a form complementary to this truncated cone element of the insert. The two truncated cone parts of the insert and the cup are therefore held in a coaxial position but are not connected since the feet maintain a minimum play between the insert and the cup. As a result the simple pushing of the insert into the cup comes to a stop almost at the same moment as the distal ends of the feet 20, 21, 22 come into contact with the free edge of the cup.

To then insert the insert into the cup by force, the surgeon applies a shock to the rod, for example by striking the top of the rod downwards in the direction of extension of the rod. Taking into account the flexibility of the feet and/or the plate, this shock simultaneously presses the insert into its final position in the cup (position represented in FIG. 2C) and releases the feet from their grip on the insert.

As the insert has been positioned by means of the device of the invention and centred perfectly relative to the cup in the position of FIG. 2B prior to the application of shock, it is not necessary for the rod to be perfectly perpendicular to the upper plane of the cup and the insert (in which planes the free edges of the cup and the insert extend respectively) during the application of this shock, the angle between the rod and the axis of the insert can in particular, as shown in FIG. 2C, have a greater value, for example 10 to 20°, without this having the least effect on the "quality" of the final insertion by force of the insert.

The relative locking of the insert in the cup is achieved by the slight difference in conicity of the inner walls 19 of the cup and 3 outer walls of the insert 1. However, it is also possible to achieve said adjustment of force in another way, for example by providing projections from the outer surface of the insert.

A first embodiment has been described above in which the surgeon applies the impaction shock by striking the rod.

It is possible, according to another advantageous embodiment, to provide at the proximal end of the rod 6 a part in the form of a pistol. Said part in the form of a pistol comprises a body 30 with a barrel 31 designed to be connected, in particular in a joined manner, to the rod 6. In the barrel 31 a cavity 32 is formed in which a plunger 33 is mounted to be movable in translation along the length of the axis of the barrel. A spring 34 is arranged at the rear of the plunger. A rod 36 joined to the plunger 33 passes through the spring and leaves the body 30 through a rear opening 50. The rod 36 enables the user, in particular by means of a ring 37 connected to the rod 36, to pull the plunger 33 to the rear thus compressing the spring 34 against a shoulder 51 of the plunger 33 until a transverse circular notch 38 is locked by clicking into an abutment 39. When the abutment 39 is locked into the notch 38, the plunger is displaced as far as possible to the rear and the spring 34 is compressed. The abutment 39 is mounted rotatably, such that a tail of a trigger 40, mounted rotatably, drives the rotation of the abutment 39 and therefore its exit from the notch 38 and lastly the release of the plunger 33. Under the effect of the charge of the precompressed spring, the plunger 33 is then displaced at high speed towards the left in FIG. 4 and hits the distal end of the cavity 32, entering into collision with the rod 6, the proximal end of which was previously introduced into an introduction channel 35 up to the distal opening 52 of the cavity 32. Locking means for the introduction of the rod into the barrel 31 can be provided so that the rod penetrates into the channel 35 but stops at the entry 52 of the cavity 32. Said locking means can for example be a circular abutment projecting laterally from the rod and abutting against the distal outlet opening of the canal 35.

The rod is then subjected to a shock which impinges on the insert made of ceramic material to insert it into the cup.

The device also comprises a grip 41 in the form of a pistol handle.

Thus the impaction force applied to the rod 6 can be determined in advance by the choice of spring 34, its rigidity and displacement path towards the rear of the plunger 33. In this way a constant impulsion force is ensured on the rod and thus a force or impaction power of the insert into the cup which is constant or substantially constant, corresponding exactly to that which is necessary to ensure the correct insertion of the insert, without the latter cracking, as was the case in the prior art where it was difficult to control the effort of the hammer. The speed imparted to the rod by the release of the plunger can be determined in advance by the choice of geometry of the constituent elements of the insertion device, in particular the spring, the plunger, the length of the tube 6 and the like.

What is claimed is:

1. A device to be received in the cotyl of a hip comprising: a cup to be received in the cotyl of a hip; an insert having an outer surface and an inner surface; gripping means gripping said insert; a rod for imparting shock, said rod designed to be held by a surgeon and for the application of an impaction shock to said insert held by said gripping means opposite the cup to be introduced therein so as to make the outer surface of said insert be in contact with said cup; and an impaction end piece fixated to said rod, said impaction end piece comprising an intermediate section in the shape of a ball and a distal section forming an impaction head having an outer surface, wherein the outer surface of said impaction head being in contact with the inner surface of said insert and said ball shaped intermediate section being in contact with said gripping means so as to form a pivot pin for an impaction end piece assembly made of said rod and said impaction end piece joined in rotation.

2. The device according to claim 1, characterized in that the pivot point of the rod and impaction end piece assembly pivots the gripping means relative to the rod and impaction end piece assembly and wherein the pivot point is located substantially in a center of a sphere defining an inner hemispherical part of the insert.

3. The device according to claim 1, characterized in that an external surface of the impaction head is designed to be applied against a base wall of a cavity of the insert, wherein the cavity is in the form of a sphere, and wherein a center of the cavity coincides with the pivot point.

4. The device according to claim 1, characterized in that the gripping means are formed by a holding grip comprising at least two feet designed to fit around the insert in an elastically releasable manner.

5. The device according to claim 4, characterized in that the holding grip comprises a base plate having a periphery from which the at least two feet project.

6. The device according to claim 5, characterized in that the base plate is pierced by a hole, an inner wall surface of which matches the form of a pivot pin formed on the rod in such a way as to enable the relative pivoting of the rod and the base plate.

7. The device according to claim 6, characterized in that a material and/or a thickness of the at least two feet and/or the base plate is such that the shock imparted by the rod simultaneously drives the insert into its final position in the cup by force and releases the at least two feet from their grip on the insert.

8. The device according to claim 6, characterized in that the hole is substantially in a center of said base plate.

9. The device according to claim 4, characterized in that there are three to five feet.

10. The device according to claim 1, characterized in that the impaction head projects laterally from a distal end of the rod, the impaction head having a distal end surface designed to match in part the form of a base of an inner cavity of the insert.

11. The device according to claim 10, characterized in that the distal end surface of the head is in the form of a dome.

12. The device according to claim 1, characterized in that means are provided for imparting to the rod a downwards shock to impact the insert into the cup with an adjustment of force to an interior of the cup, said means imparting a shock to the rod of a predetermined strength.

13. The device according to claim 1, characterized in that the gripping means grips an upper free edge of the insert.

14. The device according to claim 1, characterized in that a surface of the impaction head comes into contact with an inner surface of a hollow of the insert.

15. The device according to claim 1, characterized in that the impaction head emerges from the rod.

16. The device according to claim 1, characterized in that the pivot pin defines the pivotal relationship of the rod and impaction end piece assembly to the gripping means.

\* \* \* \* \*